Figure 1:
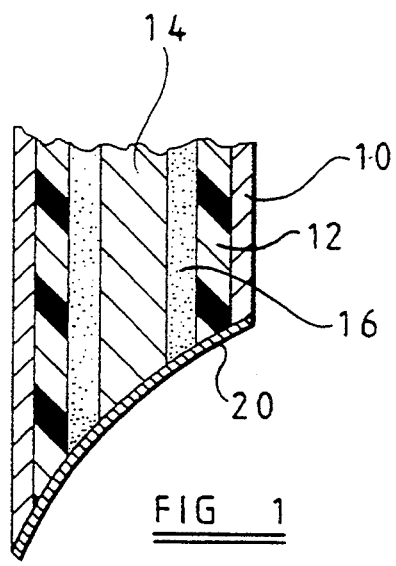

United States Patent

Band et al.

Patent Number: 5,354,449
Date of Patent: Oct. 11, 1994

[54] PH ELECTRODE

[76] Inventors: David M. Band, 88 Ditton Road, Surbiton, Surrey; David G. Penman, No. 1 Brief Street, Myatts Field, London, both of United Kingdom; Jiri Kratochvil, 3551 S. Canyon Way, Salt Lake City, Utah

[21] Appl. No.: 927,676
[22] PCT Filed: Jan. 2, 1992
[86] PCT No.: PCT/GB92/00049
§ 371 Date: Oct. 13, 1992
§ 102(e) Date: Oct. 13, 1992
[87] PCT Pub. No.: WO91/18549
PCT Pub. Date: Dec. 12, 1991

[51] Int. Cl.$^5$ ............................................. G01N 27/26
[52] U.S. Cl. ................................... 204/433; 204/435; 204/418; 204/421; 204/422
[58] Field of Search ............... 204/433, 435, 418, 419, 204/416, 421, 422, 282, 290 R

[56] References Cited

U.S. PATENT DOCUMENTS

| | | | |
|---|---|---|---|
| 3,676,319 | 7/1972 | Kirsten | 204/435 |
| 4,294,258 | 10/1981 | Bernard | 128/635 |
| 4,708,776 | 11/1987 | Roth et al. | 204/435 |
| 4,734,184 | 3/1988 | Burleigh et al. | 204/409 |
| 4,871,439 | 10/1989 | Enzer et al. | 204/401 |
| 5,223,124 | 6/1993 | Ege | 204/418 |

FOREIGN PATENT DOCUMENTS

| | | |
|---|---|---|
| 0133536 | 2/1985 | European Pat. Off. |
| 0333862 | 9/1989 | European Pat. Off. |
| 56-157849 | 12/1981 | Japan |
| 57-149953 | 9/1982 | Japan |
| 9103673 | 12/1991 | PCT Int'l Appl. |

OTHER PUBLICATIONS

Patent Abstracts of Japan, vol. 6, No. 41 (P-106) (919), published Mar. 13, 1982.
Patent Abstracts of Japan, vol. 6, No. 252 (P-161) (1130), published Dec. 10, 1982.
Eric J. Fogt et al., Simplified Procedure for Forming Polymer-Based Ion-Selective Electrodes, 57 Analytical Chemistry, 1155–1157 (1985).
EPO Search Report for PCT/GB92/00049 published May 6, 1992.

Primary Examiner—John Niebling
Assistant Examiner—Bruce F. Bell
Attorney, Agent, or Firm—Jenner & Block

[57] ABSTRACT

A pH electrode suitable for in vivo use is provided in a cannula 10, and comprises a reference electrode 14 consisting of a chloridized silver wire surrounded by a solid unbuffered internal reference material 16 comprising potassium chloride, silver chloride, citric acid and sorbitol as a hygroscopic agent. The material 16 is surrounded by a PVC sleeve 12. The tip of the cannula 10 has a pH sensitive polymer-based membrane 20 across its end. The reference material has a pH when hydrated of about 2 which is below the range of pH response of the membrane 20.

14 Claims, 1 Drawing Sheet

PH ELECTRODE

This invention relates to pH electrodes.

A conventional pH electrode consists of a membrane of glass of special composition, commonly in the form of a bulb, fused to a hollow insulating glass stem. The inside of the membrane is in contact with an internal reference solution which contains a buffering agent to maintain a constant pH. The internal reference solution is contacted by an internal reference electrode, commonly a silver or platinum conductor coated with silver/silver chloride. When the membrane is immersed in a solution, a voltage is established across the glass that is the sum of the two interface potentials which are determined by the Nernst equation and any asymmetry potential existing across the thickness of the glass membrane. The potential of this half cell is measured against an external reference electrode. In order for the electrode to be used as a pH electrode, the inner interface potential must be kept constant and the asymmetry potential calibrated out by measuring the voltage of the electrode in solutions of known pH. The function of the internal reference solution is to maintain a constant pH at the inner interface and to maintain a constant chloride activity to stabilize the internal reference electrode potential. The composition of the internal reference solution is maintained by the sealed construction of the electrode and the relative impermeability of glass to water vapor and ions.

Glass electrodes have many applications; however, their use in vivo has been restricted by a number of limitations, the most important of which is the tendency for proteins and other constituents of biological materials to coat and poison the outer sensing surface of the membrane. The fragility of the glass and the cost of manufacture can also be limitations on their use in practice.

Plastic pH membranes that are pH sensitive, either directly through the properties of the polymer itself, or through the incorporation of a ligand or ionophore selective for the hydrogen ion, have considerable advantages for biological measurements, particularly in vivo. They show biocompatibility and freedom from poisoning, are robust and cheap to make. They have, however, one important disadvantage compared with the glass electrode; the low resistance plastic membranes are relatively permeable to water vapor and to the passage of electrolytes. The dry shelf life is therefore limited by the evaporation of the internal reference solution. In use, a relatively large bulk of internal reference solution containing a buffering agent must be provided to minimize drifts in the electrode potentials due to changes in the pH of the internal reference solution caused by the movement of water and electrolytes across the membrane. Storage and miniaturization are therefore problems that have limited their applications.

In the pH sensing electrode disclosed in European Application No. A-0133 536, a silicone rubber membrane containing tridodecylamine as the ionophore is used in conjunction with a pH 4 buffer containing NaCl as an electrolyte. This pH 4 buffer corresponds substantially to the pH at which the chosen ionophore (tridodecylamine) starts to respond by exhibiting an inner membrane potential which varies with pH.

Similarly, the use of a citrate buffer in a pH monitoring sensor including a plastic membrane containing tri-n-dodecylamine as the ionophore, is disclosed in "Ion-selective sensors for assessment of the fetus" by M. O'Dowd et al, J. Biomed. Eng. 1988, Vol. 10, April, 165–169. The pH electrode disclosed in Analytical Chemistry, 1985, 57, 1155 likewise uses a tridodecylamine-containing PVC membrane in conjunction with an internal electrolyte buffered to pH 4.6. This technique of maintaining a constant internal pH requires the use of a relatively large volume of buffered electrolyte. This is not only expensive but also precludes miniaturization of the pH electrode.

Such plastic pH membranes differ from glass membranes in that the pH range over which the membranes behave according to the Nernst equation is limited and is a specific feature of the membrane composition, and in that the membranes show very low asymmetry potentials.

The object of the present invention is to exploit these last two properties to provide a novel pH electrode that is susceptible to miniaturization and useful for the accurate determination of pH in vivo (or in vitro), and which preferably has biocompatible surface characteristics, a long shelf life, and an adequate working life with low potential drift, e.g., in the region of one millivolt per day.

According to the present invention, there is provided a pH electrode comprising an internal reference electrode, a layer of internal reference material, and a pH sensitive polymer-based membrane which is most preferably biocompatible, characterized in that the membrane has a limited range of pH response, and in that the internal reference material has a pH outside the range of pH response of the membrane.

With such a pH electrode, there is no need to apply the conventional technique of using a large quantity of internal reference material (or electrolyte) which is buffered to maintain a constant pH. This is because of the finding that the internal pH can be allowed to change without affecting the potential at the internal surface of the membrane (the inner membrane potential) until the internal pH reaches a level at which the membrane responds.

In the present invention, it is preferred to use a layer of solid internal reference material comprising (a) a solid pH adjusting additive (a solid acid, e.g. an organic acid, which is preferably a pharmacologically acceptable carboxylic acid such as citric acid; or a solid alkali) in an amount such as to adjust the pH of the material (when hydrated in use) to a value outside the range of pH response of the membrane; (b) a solid electrolyte-forming material (e.g. potassium chloride); and (c) a solid reference electrode salt (e.g. silver chloride). In use, water permeates through the membrane and the solid pH adjusting additive hydrates to produce an unbuffered saturated solution. For example, in the case where citric acid is used and the membrane is of PVC with tri-n-dodecylamine as the ionophore, the solution typically has a pH of about 2. Because the solution is unbuffered, the pH can and does change during use, but it is not until the internal pH rises to about 4 that the inner membrane potential starts to vary with pH. A substantial time can elapse before this takes place, and it is this time that represents the effective working life of the pH electrode.

It is important when using a pH electrode for it to stabilize quickly upon being put into service. It is highly preferred for the internal reference material also to contain a hygroscopic material.

The inclusion of the hygroscopic material enables the internal reference material to be rapidly hydrated thereby reducing the time required for the electrode assembly to stabilize (or activate) upon being put into service.

The type and amount of the hygroscopic material can be chosen by relatively simple trial and experiment having regard to its hygroscopicity, the nature of the other ingredients, the nature of the membrane and the intended use of the electrode assembly. It is particularly preferred to use a relatively low melting point hygroscopic material, e.g. sorbitol (mp 110° C.), in a melt of which the other ingredients of the internal reference material can be dissolved or dispersed. The melt containing the other ingredients can then be introduced into a tube, such as a PVC tube, containing the reference electrode, the tube then being closed by the membrane formed in situ over the end of the tube.

The use of a low-melting hygroscopic material is particularly advantageous as it minimizes the risk of the other ingredients of the internal reference material degrading during production of the pH electrode. For example, in the case where the internal reference material contains citric acid, the low temperature of the melt does not lead to decomposition of the citric acid to citraconic acid which requires very careful handling in view of its toxic nature. Thus, the hygroscopic material preferably has a melting point which is below the decomposition temperature of the other ingredients of the internal reference material. The use of sorbitol as the hygroscopic material is particularly advantageous not only because it has a relatively low melting point, but also because it is stable, non-toxic and does not adversely affect the membrane.

Although the internal reference material is preferably a solid, it may be slightly moistened with water to accelerate full hydration when put into service in use. The desired water content thereof may conveniently be maintained by sealing the assembly before use in a hermetic package. If desired, however, the assembly may be maintained in a completely dry state by including a desiccant, e.g. silica gel, in the package.

The polymer-based membrane may be one in which (a) the polymer has an inherent permeability to hydrogen ions, or (b) an ionophore, ligand or complexing agent is incorporated in the polymer to impart such selective permeability.

Preferably, the membrane is provided across a cannula in which the reference electrode and the internal reference material are provided.

The internal reference material is chosen to be compatible with the reference electrode. Thus, in the preferred case where the reference electrode is a silver/silver chloride electrode, the internal reference material will contain silver chloride and a soluble chloride salt, e.g. a Group I chloride such as sodium chloride or potassium chloride.

The polymer-based membrane is conveniently formed of PVC incorporating tri-n-dodecylamine. In cases where the pH electrode is to be used for in vivo pH monitoring of vital fluids such as blood, the membrane is formed of a biocompatible polymer such as PVC.

The pH electrode of the present invention is primarily intended to be of the disposable type and can therefore be of a very small size consistent with providing sufficient chemicals therein to enable it to operate with acceptable stability over a relatively short period, the length of which is determined by the intended field of use. For example, in the case where the electrode assembly is intended to be used for fetal blood monitoring during childbirth, a satisfactory length of time would be about 12 hours. Typically, it is found that pH electrode having an acceptable working life span can be produced with an outer diameter of as little as 0.3 to 0.7 mm.

The pH electrode of the present invention may be used in a monitoring device for in vivo monitoring of pH in blood or other vital fluid, said device comprising a body having first and second electrodes projecting therefrom and adapted for insertion into a patient at a site where the pH of blood or other vital fluid is to be monitored, the first electrode being a reference electrode and the second electrode being the pH electrode of the present invention.

Preferably, each electrode is provided in the end of a respective helically shaped needle extending from said body so that the electrodes can be inserted through the skin of a patient to the desired depth by applying a twisting action to the body of the electrode assembly, using an appropriately shaped tool if necessary, e.g. as disclosed in U.S. Pat. No. Re 28,990. In alternative embodiments, the needles are straight, clip-like (e.g. as disclosed in European Application No. A-0007702), or outwardly splayed (e.g. as disclosed in European Application No. A-0004967.

Figure 2:
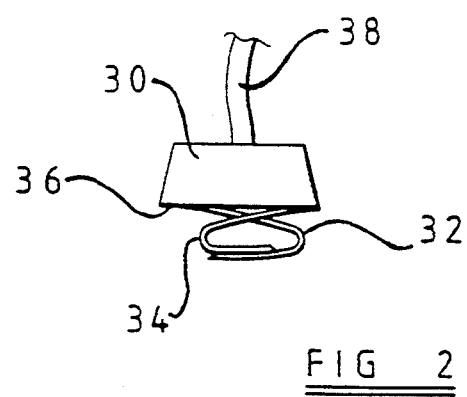

In the accompanying drawings:

FIG. 1 is a longitudinal section on a much enlarged scale of the tip of a pH electrode according to the present invention for monitoring pH, and FIG. 2 is a side view of a monitoring device including the pH electrode illustrated in FIG. 1.

Referring now to FIG. 1, the pH electrode comprises a stainless steel piercing cannula 10 of thin wall construction and having an outer diameter of 0.7 mm. Within the cannula 10, there is a PVC sleeve 12 which contacts the inner wall of the cannula 10. A chloridized silver wire having an outer diameter of 0.125 mm (to fit with clearance within the sleeve 12) provides a reference electrode 14 centrally disposed within the PVC sleeve 12 with clearance. The space between the PVC sleeve 12 and the reference electrode 14 is filled with an internal reference material 16 which in use forms an unbuffered acid electrolyte and which contains solid electrolyte solute, solid reference electrode salt and solid acid dispersed in a continuous phase of a hygroscopic material.

In one example, the internal reference material 16 comprises 54% by weight sorbitol as the hygroscopic material, 22% by weight citric acid monohydrate as the solid acid, 22% by weight sodium chloride as the solid electrolyte solute and 2% by weight silver chloride as the solid reference electrode salt. Such mixture is heated with stirring to 95° C. until it melts to a thin syrup which is used to fill the space between the reference electrode 14 and the PVC sleeve 12.

In another embodiment, sodium chloride is replaced by potassium chloride.

The tip of the cannula 10 is sharpened to provide a needle tip to assist in penetration of the skin.

The tip of the cannula 10 is dipped briefly into a solution of a polymer membrane (in this example SELECTOPHORE as supplied by Fluka Ltd) in tetrahydrofuran which is free of stabilizers. This membrane material is based on PVC which contains tri-n-dodecylamine as a hydrogen ion carrier. Dipping of the needle tip of the assembly into the membrane solution followed by drying results in the formation of a membrane 20 across the bevel. The membrane 20, being of PVC, is bonded firmly to the PVC sleeve 12 and contacts the electrolyte 16. Typically, the membrane 20 has a thickness of about 0.1–0.2 mm.

The membrane 20 has a relatively restricted effective working pH range of about 4 to 8, but this is acceptable in fetal blood monitoring situations. The membrane 20 is also permeable to water vapor so that, when it is disposed in an aqueous liquid, e.g. blood, water can permeate through the membrane 20 and hydrate the internal reference material 16. Passage of water across the membrane is accelerated by the presence of the hygroscopic material within the electrode, thus enabling the electrode to stabilize quickly upon being put into service. The arrangement is such that, over the desired effective working life of the electrode assembly, the electrolyte remains saturated with sodium chloride, and citric acid and silver chloride is always present. Typically, the electrolyte, after hydration, has a pH of about 2 which is below that at which the inner membrane potential starts to respond to changes in internal pH. Thus, the potential at the inner surface of the membrane 20 remains acceptably constant for the intended effective operating life of the electrode assembly (typically about 12 hours). The inner reference electrode potential also remains acceptably constant because, throughout the intended effective operating life of the electrode assembly, there is always silver, silver chloride and a saturated chloride solution in contact with the electrode.

The above-described pH electrode can be used in conjunction with a reference electrode in the monitoring device illustrated in FIG. 2. Such device is intended for fetal pH monitoring during childbirth and comprises a synthetic plastic body 30 which carries first and second electrodes 32 and 34. The electrodes 32 and 34 are of helical shape mutually arranged about a common axis so as to define a double start helix. The monitoring device can be fixed in position by turning it in a clockwise direction to cause the sharpened tips of the electrodes 32 and 34 to penetrate the skin on the head of the fetus so as to be in contact with the fetal blood. The depth of insertion is limited by the engagement of the underside surface 36 of the body against the skin. The first electrode 32 is a reference electrode formed by threading an insulated silver wire through a needle, and securing it into position using a medical grade epoxy resin applied to the tip of the needle so that it runs back up the needle tube. After curing, wire and excess epoxy resin is cut off flush with the bevel of the needle, the exposed silver at the end surface of the silver wire is chloridized, and then the bevel of the needle is touched onto the surface of a solution of a biocompatible polyurethane polymer, e.g. TECOFLEX in tetrahydrofuran. The resultant layer of resin serves to prevent the deposition of proteins on the electrode as a result of the protein-coagulating effect of silver.

The second electrode 34 is a pH sensing electrode of the type described above with reference to FIG. 1.

The monitoring device of FIG. 2 further includes electrical leads 38 which extend to a remote location for attachment to a pH meter which is a very high input resistance voltmeter scaled in units of the Nernst equation, with a facility for backing off the standing voltage of the pH cell so that pH changes can be displayed.

In another embodiment (not shown), a pH electrode in accordance with the invention may be prepared by forming a silver/silver chloride electrode on the end of a conducting wire, which may be a silver wire (or a stainless steel wire or other material coated with silver) and chloridized over an end portion. The chloridized end portion is coated with a thin layer of electrical insulating material, e.g. PVC, the end is cut off and the exposed area is rechloridized, so that the end forms a silver/silver chloride electrode area. That area and a small part of the insulated portion adjacent thereto may then be dipped into a mixture of equal parts of finely ground potassium chloride and citric acid with a 1% addition of silver chloride, the mixture being warmed until the citric acid melts, the solidified layer formed being the internal reference material. This layer is then coated with a pH sensitive membrane, e.g. PVC (to bond with the layer of insulation) containing a plasticizer and the pH sensitive ionophore or ligand, e.g. tri-n-dodecylamine. The membrane may also contain potassium tetraphenylborate or potassium para-chlorotetraphenylborate as additives without impairing the compatibility with body-tissue or fluid.

Such electrodes have a typical working life of two days and their potential in a phosphate buffer of 6.84 pH will drift by around one millivolt per day. They can be sterilized and stored dry in sterile packaging until use and have a longer shelf life than existing fluid filled PVC/ionophore pH electrodes, which eventually desiccate due to the passage of water vapor through the PVC/ionophore membrane.

Although electrodes in accordance with the invention will generally be regarded as disposable and used only once each, such an electrode may be dried after use and stored until required again.

In a further embodiment, a pH electrode in accordance with the invention may be prepared by forming a silver/silver chloride internal reference electrode on one face of a silver plate (or a plate of stainless steel or other material coated on one face with silver) by chloridizing, coating with a layer of potassium chloride/citric acid/silver chloride mixture prepared as above, and encapsulating the remainder of the plate in insulating material after attaching an electrically conducting lead to the plate.

In a still further embodiment, a pH electrode in accordance with the invention may be prepared by forming a silver film within a masked area of a plastic or ceramic substrate, chloridizing the exposed surface of the silver film, coating the chloridized surface with a layer of potassium chloride/citric acid/silver chloride prepared as above, and covering that layer with a pH sensitive membrane prepared as above.

Any of the aforementioned methods of preparing a pH electrode in accordance with the invention may be modified by mixing the mixture of finely ground potassium chloride/citric acid/silver with diacetone acrylamide polymer in a ration of 60% salt mixture; 30% of the polymer by weight. The advantage of using diacetone acrylamide lies in:

1. Lowering of the processing temperature of the internal reference material to 54°–56° C. which is the melting point of the polymer;
2. The plasticizing effect of the polymer additive resulting in the viscosity reduction of the warmed mixture; and
3. The water-retaining properties of diacetone acrylamide.

Better rheological properties obtained with this additive are especially desirable in the construction of pH sensitive devices based on planar processing technologies, i.e. thick film/thin film pH sensors and pH sensitive field effect transistors. In these sensing devices, it is often required to dispense a small volume of the internal reference material into photolithographically patterned microwells and this cannot be done by conventional coating techniques.

We claim:

1. A pH electrode comprising an internal reference electrode, a layer of internal reference material and a pH sensitive polymer-based membrane, characterized in that the membrane has a limited range of pH response, and in that the internal reference material has a pH outside the range of pH response of the membrane.

2. A pH electrode as claimed in claim 1, wherein the internal reference material is solid.

3. A pH electrode as claimed in claim 1, wherein the internal reference material has a pH which is below the range of pH response of the membrane.

4. A pH electrode as claimed in claim 1, wherein the internal reference material comprises a mixture of a solid pH adjusting additive, a solid electrolyte-forming material and a solid reference electrode salt.

5. A pH electrode as claimed in claim 1, wherein the internal reference material contains a hygroscopic material.

6. A pH electrode as claimed in claim 5, wherein the hygroscopic material has a melting point which is below the decomposition temperature of the other ingredients of the internal reference material.

7. A pH electrode as claimed in claim 6, wherein the hygroscopic material is sorbitol.

8. A pH electrode as claimed in claim 1, wherein the internal reference electrode is a silver/silver chloride reference electrode, and the internal reference material comprises silver chloride, a water-soluble chloride, a pharmacological carboxylic acid, and sorbitol.

9. A pH electrode as claimed in claim 8, wherein the pharmacological carboxylic acid is citric acid.

10. A pH electrode comprising an internal reference electrode, a layer of internal reference material comprising a hygroscopic material, and a pH sensitive polymer-based membrane, characterized in that the membrane has a limited range of pH response, and in that the internal reference material has a pH outside the range of pH response of the membrane.

11. A pH electrode as claimed in claim 10, wherein the hygroscopic material has a melting point which is below the decomposition temperature of the other ingredients of the internal reference material.

12. A pH electrode as claimed in claim 11, wherein the hygroscopic material is sorbitol.

13. A pH electrode as claimed in claim 10, wherein the internal reference electrode is a silver/silver chloride reference electrode, and the internal reference material comprises silver chloride, a water-soluble chloride, a pharmacological carboxylic acid, and sorbitol.

14. A pH electrode as claimed in claim 13, wherein the pharmacological carboxylic acid is citric acid.

* * * * *